United States Patent [19]

Rowsell et al.

[11] 4,070,449

[45] Jan. 24, 1978

[54] COMPOUNDS HAVING A PHYSIOLOGICAL COOLING EFFECT AND COMPOSITIONS CONTAINING THEM

[75] Inventors: David G. Rowsell, Staines; Roger Hems, Maidenhead, both of England

[73] Assignee: Wilkinson Sword Limited, London, England

[21] Appl. No.: 381,097

[22] Filed: July 20, 1973

[30] Foreign Application Priority Data

Oct. 24, 1972 United Kingdom .............. 49039/72

[51] Int. Cl.$^2$ ........................ A61K 7/16; A61K 31/10
[52] U.S. Cl. ................................... 424/45; 131/120; 132/89; 252/32; 252/522; 424/49; 424/56; 424/57; 424/65; 424/70; 424/73; 424/148; 424/156; 424/168; 424/230; 424/329; 424/337; 424/358; 424/315; 426/3; 426/590
[58] Field of Search .......................... 424/337, 315, 45

[56] References Cited

U.S. PATENT DOCUMENTS

| 2,001,046 | 5/1935 | Welch | 424/343 |
|---|---|---|---|
| 2,142,162 | 1/1939 | Werntz | 260/513 R |
| 2,187,339 | 1/1940 | Werntz | 260/513 R |
| 2,374,983 | 5/1945 | Simo | 260/513 R |
| 2,926,118 | 2/1960 | Mahan | 424/337 |
| 2,957,799 | 10/1960 | Goodhue et al. | 424/337 |
| 3,103,465 | 9/1963 | Goodhue et al. | 424/337 |
| 3,511,914 | 5/1970 | Wolkoff et al. | 424/343 |
| 3,644,653 | 2/1972 | Tcheitcheff | 424/358 |
| 3,853,895 | 12/1974 | Lamm et al. | 260/294.9 |
| 3,899,478 | 8/1975 | Fleckenstein et al. | 260/156 |
| 3,907,769 | 9/1975 | Dehnert et al. | 260/156 |
| 3,947,463 | 3/1976 | Fleckenstein et al. | 260/294.8 G |

FOREIGN PATENT DOCUMENTS

| 2,230,392 | 6/1972 | Germany. |
| 1,377,506 | 12/1974 | United Kingdom. |
| 1,420,411 | 1/1976 | United Kingdom. |

OTHER PUBLICATIONS

Remington's Pharmaceutical Sciences, 13th Edition, (1965), p. 855.

Wilson et al., Textbook of Organic Medicinal and Pharmaceutical Chemistry, 4th Edition, (1962), pp. 111–112.

Chemical Abstracts 8th Collective Index, (1967–1971) vols. 66–75, pp. 18623s–18627s.

Chemical Abstracts 7th Collective Index, (1962–1966) vols. 56–65, pp. 13780s–13782s.

Bernstein, et al., J. Am. Chem. Soc. 69, 1151–1158, (1947).

*Primary Examiner*—Leonard Schenkman
*Attorney, Agent, or Firm*—Leydig, Voit, Osann, Mayer & Holt, Ltd.

[57] ABSTRACT

Compositions are disclosed having a physiological cooling action on the skin. The compositions contain as the active ingredient certain acyclic secondary and tertiary sulphoxides and sulphones.

6 Claims, No Drawings

COMPOUNDS HAVING A PHYSIOLOGICAL COOLING EFFECT AND COMPOSITIONS CONTAINING THEM

FIELD OF THE INVENTION

This invention relates to topical and other compositions having a physiological cooling effect on the skin and on the mucous membranes of the body, particularly the nose, mouth, throat and gastrointestinal tract.

BACKGROUND OF THE INVENTION

Menthol is well known for its physiological cooling effect on the skin and mucous membranes of the mouth and has been extensively used as a flavouring agent (menthol being a major constituent of oil of peppermint) in foodstuffs, beverages, dentifrices, mouthwashes, etc. and as a component in a wide range of toiletries, liniments and lotions for topical application. Menthol is also a well known tobbacco additive for producing a "cool" sensation in the mouth when smoking.

It is well established that the "cooling" effect of menthol is a physiological effect due to the direct action of menthol on the nerve endings of the human body responsible for the detection of hot or cold and is not due to latent heat of evaporation. It is believed that the menthol acts as a direct stimulus on the cold receptors at the nerve endings which in turn stimulate the central nervous system.

Although menthol is well established as a physiological coolant its use, in some compositions, is circumscribed by its strong minty odour and its relative volatility.

Other compounds have been mentioned in the art as having a physiological cooling effect e.g. 2,4,6-trimethyl-4-heptanol (Parfums-Cosmetiques-Savons, May 1956, pages 17-20) and N,N-diethyl-2-ethylbutanamide (French Pat. No. 1,572,332).

OBJECTS OF INVENTION

The object of the present invention is to provide other compounds having a physiological cooling effect similar to that obtained with menthol but without its attendant disadvantages.

It is a further object of the invention to provide ingestible, topical and other compositions containing such compounds in an amount to provide a physiological cooling effect when such compositions are used in or by the human body.

It is a further object to provide a method of stimulating the cold receptors of the body using agents other than menthol.

SUMMARY OF INVENTION

According to the invention we have found a group of acyclic sulphones and sulphoxides which are capable of stimulating the cold receptors of the nervous system of the body.

DETAILED DESCRIPTION OF INVENTION

The compounds having this physiological cooling effect and usable according to this invention are aliphatic, acyclic sulphones and sulphoxides of the formula:

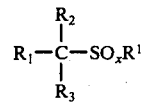

where
$R_1$ is H or $C_1$-$C_5$ alkyl;
$R_2$ is $C_1$-$C_6$ alkyl;
$R_3$ is $C_1$-$C_8$ alkyl;
$R_1$, $R_2$ and $R_3$ together provide a total of from 3-15 carbon atoms preferably 5-10 carbon atoms;
$R^1$ is alkyl, optionally containing hydroxy, carboxy, or alkylcarboxy substituents, $R_1$, $R_2$, $R_3$ and $R^1$ together providing a total of from 6-18 carbon atoms; and
$x$ is 1 or 2.

Preferred compounds are sulphoxides and sulphones of the formula:

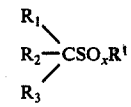

where $x$ is 1 or 2, $R^1$ is alkyl and contains up to 8 carbon atoms, $R_1$ is hydrogen or $C_1$-$C_4$ alkyl, and $R_2$ and $R_3$ are each $C_1$-$C_6$ alkyl, $R^1$, $R_1$, $R_2$ and $R_3$ together providing a total of from 8-14 carbon atoms.

Generally speaking the sulphoxides, i.e. compounds where $x$ is 1, are to be preferred over the corresponding sulphones, i.e. the compounds where $x$ is 2.

Broadly speaking, therefore, the invention provides compositions, in particular ingestible compositions and compositions for topical application, capable of stimulating the cold receptors of the nervous system of the human body comprising an effective amount of a cold receptor stimulant and a carrier therefor, the stimulant comprising one or more of the above defined sulphoxides or sulphones.

The sulphoxides and sulphones used in the invention may be readily prepared by conventional methods, such as by the oxidation of the corresponding sulphide, e.g. with hydrogen peroxide in glacial acetic acid.

Many of the compounds used in this invention exhibit optical isomerism and, depending on the starting materials and the methods used, the compounds used in this invention may be isomerically pure, i.e. consisting of one optical isomer, or they may be a mixture of isomers. In those compounds where optical isomerism occurs the degree of cooling produced by the compounds will differ as between isomers, in which case one or other isomer will be preferred.

The compounds of the above formulae find utility in a wide variety of compositions for consumption by or application to the human body. Broadly speaking, these compositions can be divided into comestible and topical compositions, both terms being taken in their broadest possible sense. Thus comestible is to be taken as including not only foodstuffs and beverages taken into the mouth and swallowed, but also other orally ingested compositions taken for reasons other than their nutritional value, e.g. indigestion tablets, antacid preparations, laxatives etc. Comestible compositions are also to be taken to include edible compositions taken by mouth, but not necessarily swallowed, e.g. chewing gum. Topical compositions are to be taken as including not only compositions such as perfumes, powders and other toiletries, lotions, liniments, oils and ointments applied to the external surfaces of the human body, whether for medical or other reasons, but also compositions applied to, or which, in normal usage, come in contact with, internal mucous membranes of the body, such as those of the nose, mouth, or throat, whether by direct or indirect application or inhalation, and thus include nasal and throat sprays, dentifrice, mouthwash and gargle compositions. Also included within the present invention are toilet articles such as cleaning tissues and toothpicks impregnated or coated with the active cooling compound.

A further class of compositions included within the scope of this invention are tobacco and associated articles e.g. pipe and cigarette filters, especially filter tips for cigarettes.

The compositions of this invention will contain an amount of the sulphone or sulphoxide sufficient to stimulate the cold receptors in the areas of the skin or mucous membrane with which the compositions come into contact and thereby promote the desired cold sensation. The degree and longevity of cooling sensation varies from compound to compound and therefore the quantity of stimulant used in each composition will vary widely. As a guide, it may be said that, with the more active compounds of the invention, a significant cooling sensation is achieved upon application to the skin of as little as 0.05 ml. of a 0.5 weight percent solution of the active ingredient in ethanol. For the less active compounds a significant cooling effect is achieved only with more concentrated solutions, e.g. containing 5.0% by weight or more of the active ingredient.

Typical sulphoxides and sulphones falling within the above formulae and utilisable in the compositions of this invention are indicated in the following Table together with an indication of their relative activities as a stimulant for the cold receptors of the nervous system of the human body. The greater the number of stars, the greater the activity, i.e. the greater the cooling effect produced by application of a given quantity of the compound.

Table

| x | $R_1$ | $R_2$ | $R_3$ | $R^1$ | Activity |
|---|---|---|---|---|---|
| 1 | $CH_3$ | $C_2H_5$ | $C_2H_5$ | $-CHCH_2CH_3$ with $C_2H_5$ | * * * |
| 1 | " | $CH_3$ | iso-$C_3H_7$ | n-$C_6H_{13}$ | * * * |
| 1 | $C_2H_5$ | $C_2H_5$ | $C_2H_5$ | n-$C_4H_9$ | * * * |
| 1 | H | n-$C_6H_{13}$ | iso-$C_3H_7$ | n-$C_3H_7$ | * * * |
| 1 | $CH_3$ | $C_2H_5$ | n-$C_3H_7$ | iso-$C_3H_7$ | * * * |
| 1 | H | iso-$C_3H_7$ | n-$C_4H_9$ | n-$C_4H_9$ | * * * |
| 1 | " | " | " | n-$C_6H_{13}$ | * * * |
| 1 | $CH_3$ | $C_2H_5$ | n-$C_3H_7$ | n-$C_8H_{17}$ | * * |
| 1 | " | " | " | $-CHCH_2CH_3$ with $C_2H_5$ | * * |
| 1 | " | " | $C_2H_5$ | iso-$C_3H_7$ | * * |
| 1 | " | " | " | n-$C_4H_9$ | * * |
| 1 | " | " | " | n-$C_6H_{13}$ | * * |
| 1 | " | " | " | $-CH(CH_2)_2CH_3$ with $CH_3$ | * * |
| 1 | " | " | " | $-CH(CH_2)_3CH_3$ with $CH_3$ | * * |
| 1 | " | " | " | $-CHCH_2CH_3$ with $C_2H_5$ | * * |
| 1 | " | " | n-$C_3H_7$ | n-$C_5H_{11}$ | * * |
| 1 | " | " | " | sec-$C_4H_9$ | * * |
| 1 | H | iso-$C_4H_9$ | iso-$C_4H_9$ | sec-$C_4H_9$ | * * |
| 1 | " | $CH_3$ | iso-$C_3H_7$ | " | * * |
| 1 | " | sec-$C_4H_9$ | " | n-$C_4H_9$ | * * |
| 1 | iso-$C_3H_7$ | $CH_3$ | $CH_3$ | sec-$C_4H_9$ | * * |
| 1 | H | sec-$C_4H_9$ | n-$C_3H_7$ | n-$C_4H_9$ | * * |
| 1 | " | iso-$C_3H_7$ | n-$C_3H_7$ | " | * * |
| 1 | n-$C_3H_7$ | n-$C_3H_7$ | " | n-$C_3H_7$ | * * |
| 1 | iso-$C_4H_9$ | $CH_3$ | " | " | * * |
| 1 | iso-$C_5H_{11}$ | " | " | " | * * |
| 1 | $CH_3$ | $C_2H_5$ | $C_2H_5$ | $CH_2CH_2CO_2C_2H_5$ | * |
| 1 | " | " | " | $CH_2CH_2OH$ | * |
| 1 | H | iso-$C_4H_9$ | iso-$C_4H_9$ | n-$C_3H_7$ | * |
| 1 | " | " | " | $CH_2CH_2OH$ | * |
| 1 | " | $C_2H_5$ | n-$C_4H_9$ | n-$C_4H_9$ | * |
| 1 | " | " | " | iso-$C_4H_9$ | * |
| 1 | " | " | " | $CH_2CH_2OH$ | * |
| 1 | " | " | n-$C_3H_7$ | iso-$C_3H_7$ | * |
| 1 | " | " | " | $CH_3$ | * |
| 1 | H | $C_2H_5$ | n-$C_3H_7$ | n-$C_8H_{17}$ | * |
| 1 | " | " | " | $CHCH_2CH_3$ with $C_2H_5$ | * |
| 1 | " | $CH_3$ with $CH_2CHC_2H_5$ | $C_2H_5$ | tert.-$C_4H_9$ | * |
| 1 | " | $CH_3$ | " | sec-$C_4H_9$ | * |
| 1 | " | " | " | iso-$C_5H_{11}$ | * |
| 1 | $CH_3$ | $C_2H_5$ | n-$C_3H_7$ | $CH_3$ | * |
| 2 | " | " | $C_2H_5$ | n-$C_6H_{13}$ | * |
| 2 | H | sec-$C_4H_9$ | n-$C_3H_7$ | n-$C_4H_9$ | * |
| 2 | " | iso-$C_3H_7$ | " | " | * |
| 2 | $C_2H_5$ | $C_2H_5$ | $C_2H_5$ | " | * |

Table -continued

| x | R₁ | R₂ | R₃ | R¹ | Activity |
|---|----|----|----|----|----------|
| 2 | H | iso-C₃H₇ | n-C₆H₁₃ | n-C₃H₇ | * |

In formulating the compositions of this invention the sulphoxide or sulphone will usually be incorporated into a carrier which may be completely inert or which may be or contain other active ingredients. A wide variety of carriers will be suitable, depending upon the end use of the composition, such carriers including solids, liquids, emulsions, foams and gels. Typical carriers for the sulphoxides and sulphones include aqueous or alcoholic solutions; oils and fats such as hydrocarbon oils, fatty acid esters, long chain alcohols and silicone oils; finely divided solids such as starch or talc; cellulosic materials such as paper tissue; tobacco; low-boiling hydrocarbons and halohydrocarbons used as aerosol propellants; gum and natural or synthetic resins.

In most compositions according to the invention the carrier will be or contain as an adjuvant one or more of the following: an antacid, antiseptic or analgesic, a flavourant, colourant, or odourant, or a surfactant.

The following illustrate the range of compositions into which the compounds of this invention can be incorporated:

1. Edible or potable compositions including alcoholic and non-alcoholic beverages, confectionery, chewing gum; cachous; ice cream; jellies;
2. Toiletries including after shave lotions, shaving soaps, creams and foams, toilet water, deodorants and antiperspirants, "solid colognes", toilet soaps, bath oils and salts, shampoos, hair oils, talcum powders, face creams, hand creams, sunburn lotions, cleansing tissues, dentifrices, toothpicks, mouthwashes, hair tonics, eyedrops;
3. Medicaments including antiseptic ointments, pile ointments, liniments, lotions, decongestants, counter-irritants, cough mixtures, throat lozenges, antacid and indigestion preparations, oral analgesics;
4. Tobacco preparations including cigars, cigarettes, pipe tobacco, chewing tobacco and snuff; tobacco filters, especially filter tips for cigarettes.
5. Miscellaneous compositions such as water soluble adhesive compositions for envelopes, postage stamps, adhesive labels etc.

Particular preparations according to the invention are discussed in more detail below.

Edible and Potable Compositions

The edible and potable compositions of this invention will contain the active cooling compound in combination with an edible carrier and usually a flavouring or colouring agent. The particular effect of the compounds of the invention is to create a cool or fresh sensation in the mouth, and in some cases, even in the stomach, and therefore they find particular utility in sugar-based confectionery such as chocolate, boiled sweets, mints, and candy, in ice cream and jellies and in chewing gum. The formulation of such confections will be by ordinary techniques and according to conventional recipes and as such forms no part of this invention. The active compound will be added to the recipe at a convenient point and in amount sufficient to produce the desired cooling effect in the final product. As already indicated, the amount will vary depending upon the particular compound, the degree of cooling effect desired and the strength of other flavourants in the recipe. For general guidance, however, amounts in the range 0.05 to 2.5% by weight based on the total composition will be found suitable.

Similar considerations apply to the formulation of beverages. Generally speaking the compounds will find most utility in soft drinks e.g. fruit squashes, lemonade, cola etc., but may also be used in alcoholic beverages. The amount of compound used will generally be in the range 0.02 to 0.5% by weight based on the total composition.

Toiletries

Because of the cooling sensation imparted to the skin, a major utility of the compounds of this invention will be in a wide range of toilet preparations and toilet articles. The particular preparations discussed below are to be taken as exemplary.

A major utility will be in after shave lotions, toilet water, etc., where the compound will be used in alcoholic or aqueous alcoholic solution, such solutions usually also containing a perfume or mild antiseptic or both. The amount of sulphoxide or sulphone added to the formulation will usually be in the range 0.1 to 5.0% by weight based on the total composition.

Another field of utility will be in soaps, shampoos, bath oils etc. where the compound will be used in combination with an oil or fat or a natural or synthetic surfactant e.g. a fatty acid salt or a lauroylsulphate salt, the composition usually also containing an essential oil or perfume. The range of soap compositions will include soaps of all kinds e.g. toilet soaps, shaving soaps, shaving foams etc. Usually the active compound will be added to the formulation in amount of from 0.1 to 5.0% by weight.

A further class of toilet compositions into which the compounds of this invention may be incorporated includes cosmetic creams and emollients, such creams and emollients usually comprising a base emulsion and optionally a range of ingredients such as wax, preservative, perfume, antiseptics, astringents, pigments etc. Also included within this class are lipstick compositions such compositions usually comprising an oil and wax base into which the compound can be incorporated along with the formulation of such compositions, apart from the incorporation of the active compound, usually in an amount of from 0.05 to 5.0% by weight, is conventional.

Compositions or oral hygiene containing the cold receptor stimulants of this invention include mouthwash, gargle and dentifrice compositions. The first two may be considered together and will usually comprise an aqueous, alcoholic or aqueous-alcoholic solution of an antiseptic often coloured or flavoured for palatability, to which the compound is added in an amount of from 0.05 to 0.5% by weight.

Dentifrice compositions may be of the solid block, powder, paste or liquid type and will usually comprise a finely divided abrasive or polishing material, e.g. precipitated chalk, silica, magnesium silicate, aluminium hydroxide or other similar materials well known in the art, and a detergent of foaming agent. Optional ingredients which may also be included are flavouring agents and colourants, antiseptics, lubricants, thickeners, emulsifiers or plasticizers. The amount of active compound added in such compositions will generally be from 0.1 to 2.5% by weight based on the total composition.

Medicaments

Because of their cooling effect on the skin and on the mucous membranes of the mouth, throat and nose and of the gastrointestinal tract the compounds of this invention may be used in a variety of oral medicines, nasal and throat sprays, and topical compositions, particularly where a counter-irritant is required. In particular the compounds of the invention may be formulated into antacid and indigestion remedies, in particular those based on sodium bicarbonate, magnesium oxide, calcium or magnesium carbonate, aluminium or magnesium hydroxide or magnesium trisilicate. In such compositions the compounds will usually be added in an amount of from 0.05 to 1.0% by weight.

The compounds of the invention may also be included in oral analgesic compositions e.g. with acetylsalicyclic acid or its salts, and in nasal decongestants e.g. those containing ephedrine.

Tobacco Preparations

The compounds of this invention may be incorporated directly into tobacco to give a cool effect when smoking but without the attendant strong and characteristic odour which is associated with mentholated tobacco and cigarettes. However, a more advantageous utilisation of the compounds of this invention is in pipe or cigarette filters, in particular, filter tipped cigarettes. The pad of filter material, which may be of any of the well known types, e.g. cellulose acetate, paper, cotton α-cellulose or asbestos fibers, is simply impregnated with an alcoholic solution of the sulphone or sulphoxide and dried to deposit the compound in the filter pad. The effect is to give a pleasant cool sensation in the mouth when the cigarette is smoked. As little as 0.05 mg. of the compound is effective.

Compositions according to the invention are illustrated by the following Examples.

EXAMPLE 1

After Shave Lotion

An after shave lotion was prepared according to the following recipe by dissolution of the ingredients in the liquid and cooling and filtering:

| | | |
|---|---|---|
| Denatured Ethanol | 75% | |
| Diethylphthalate | 1.0% | |
| Propylene Glycol | 1.0% | |
| Lactic Acid | 1.0% | |
| Perfume | 3.0% | |
| Water | to 100% | |

Into a sample of the base lotion was added 2.0% by weight based on the weight of the sample of 3-methylpent-3-yl isopropyl sulphoxide.

When the final solution was applied to the face a clearly noticeable cooling effect became apparent after a short interval of time.

EXAMPLE 2

Toilet Water

A toilet water was prepared according to the following recipe:

| | | |
|---|---|---|
| Denatured Ethanol | 75.0% | |
| Perfume | 5.0% | |
| Water | to 100% | |

To the recipe was added 3.0%, based on the total composition, of 3-methylhex-3-yl isopropyl sulphoxide.

As with the after shave lotion, a cooling effect was clearly noticeable on the skin well after the termination of any cooling effect attributable to the evaporation of the alcoholic carrier.

EXAMPLE 3

Eye Lotion

An eye lotion was prepared containing the following ingredients:

| | | |
|---|---|---|
| Witch Hazel | 12.95 | % |
| Boric Acid | 2.00 | % |
| Sodium Borate | 0.50 | % |
| Allantoin | 0.05 | % |
| Salicylic Acid | 0.025 | % |
| Chlorobutol | 0.02 | % |
| Zinc Sulphate | 0.004 | % |
| Water | to 100 | % |

To the formulation was added 0.005%, based on the total composition, of 3-methylpent-3-yl 2-ethylcarboxyethyl sulphoxide. When used to bathe the eyes a cool fresh sensation is apparent on the eyeball and eyelids.

EXAMPLE 4

Antiseptic Ointment

An ointment was prepared according to the following formulation:

| | |
|---|---|
| Cetyltrimethyl ammonium bromide | 4.0% |
| Cetyl Alcohol | 6.0% |
| Stearyl Alcohol | 6.0% |
| White Paraffin | 14.0% |
| Mineral Oil | 21.0% |
| Water | to 100% |

The ingredients were mixed, warmed to 40° C and emulsified in a high speed blender. Added to the mixture during blending was 3.0% of 3-methylhex-3-yl n-octyl sulphoxide.

The final ointment when applied to the skin gave rise to a cooling effect.

EXAMPLE 5

Antipruritic Ointment

The following ingredients were warmed together to form a homogeneous melt:

| | |
|---|---|
| Methyl Salicylate | 50.0% |
| White Beeswax | 25.0% |
| Anhydrous Lanolin | 25.0% |

To the melt was added 3.0% of 3-methylpent-3-yl pent-2-yl sulphoxide and the mixture then allowed to solidify. A soft ointment resulted having a soothing effect on the skin accompanied by a cooling effect.

EXAMPLE 6

Cleansing Tissue

A cleansing liquid was prepared having the formulation:

| Triethanolamine Lauryl Sulphate | 1.0 % |
|---|---|
| Glycerol | 2.0 % |
| Perfume | .95 % |
| Water | to 100 % |

To this liquid was added 3.0% of n-hexyl 2,3-dimethylbut-3-yl sulphoxide. A paper tissue was then soaked in the liquid.

When the impregnated tissue was used to wipe the skin a fresh cool sensation developed on the skin after a short interval.

EXAMPLE 7

Cigarette Tobacco

A proprietary brand of cigarette tobacco was sprayed with an ethanolic solution of hex-3-yl isopropyl sulphoxide and was rolled into cigarettes each containing approximately 0.05 mg. of active compound. Smoking the impregnated cigarettes produced a cool effect in the mouth characteristic of mentholated cigarettes but without any attendant odour other than that normally associated with tobacco.

Impregnation of the filter tip of a proprietary brand of tipped cigarette with 0.01 mg. of the same sulphoxide produced a similar effect.

EXAMPLE 8

Toothpaste

The following ingredients were mixed in a blender:

| Dicalcium phosphate | 48.0% |
|---|---|
| Sodium lauryl sulphate | 2.5% |
| Glycerol | 24.8% |
| Sodium carboxymethyl cellulose | 2.0% |
| Citrus flavourant | 1.0% |
| Sodium saccharin | 0.5% |
| Water | to 100% |

Shortly before completion of the blending operation 0.5% by weight of 3-methylpent-3-yl n-hexyl sulphoxide was added to the blender.

When applied as a toothpaste a pleasant cooling effect is noticed in the mouth.

EXAMPLE 9

After Shave Lotion

An after shave lotion was prepared according to the following recipe by dissolution of the ingredients in the liquid and cooling and filtering:

| Denatured Ethanol | 75% |
|---|---|
| Diethyl Phthalate | 1.0% |
| Propylene Glycol | 1.0% |
| Lactic Acid | 1.0% |
| Perfume | 3.0% |
| Water | to 100% |

Into the base lotion was added 3% by weight based on the total composition of n-butyl 3-methylhept-4-yl sulphone.

When the final lotion is applied to the face a clearly noticeable cooling effect becomes apparent after a short interval of time.

EXAMPLE 10

Eye Lotion

An eye lotion was prepared containing the following ingredients:

| Witch Hazel | 12.95 % |
|---|---|
| Boric Acid | 2.00 % |
| Sodium Borate | 0.50 % |
| Allantoin | 0.05 % |
| Salicylic Acid | 0.025 % |
| Chlorobutol | 0.02 % |
| Zinc Sulphate | 0.004 % |
| Water | to 100 % |

To the formulation was added 0.005%, based on the total composition of 2-methylnon-3-yl propyl sulphone. When used to bathe the eyes a cool fresh sensation is apparent on the eyball and eyelids.

EXAMPLE 11

Toothpaste

The following ingredients were mixed in a blender:

| Dicalcium Phosphate Dihydrate | 40% |
|---|---|
| Sodium Lauryl Sarcosinate | 1.5% |
| Glycerol | 30% |
| Sodium Carboxymethyl Cellulose | 1.5% |
| Saccharin Sodium | 0.2% |
| Sodium Benzoate | 0.2% |
| Water | 26.6% |

Shortly before completion of the blending operation 0.5% by weight of n-butyl 2-methylhex-3-yl sulphone was added to the blender.

When applied as a toothpaste, a cooling effect is noticed in the mouth.

EXAMPLE 12

Soft Sweet

Water was added to icing sugar at 40° C to form a stiff paste. 0.1% of 4-n-propylhept-4-yl n-propyl sulphoxide was then stirred into the paste and the mixture allowed to set. A soft sweet mass resulted having the characteristic cooling effect in the mouth of peppermint but without the minty flavour or odour.

EXAMPLE 13

Antiseptic Ointment

An ointment was prepared according to the following formulation:

| Cetyltrimethyl ammonium bromide | 4.0% |
|---|---|
| Cetyl alcohol | 6.0% |
| Stearyl alcohol | 6.0% |
| White Paraffin | 14.0% |
| Mineral Oil | 21.0% |
| Water | to 100% |

The ingredients were mixed, warmed to 60° C and emulsified in a high-speed blender. Added to the mixture during blending was 4% of n-hexyl 3-methylpent-3-yl sulphone.

The final ointment when applied to the skin gave rise to a marked cooling effect.

EXAMPLE 14

Aerosol Shaving Soap

An aerosol shaving soap composition was formulated according to the following recipe:

|  |  |
|---|---|
| Stearic Acid | 6.3% |
| Lauric Acid | 2.7% |
| Triethanolamine | 4.6% |
| Sodium Carboxymethyl Cellulose | 0.1% |
| Sorbitol | 5.0% |
| Water | to 100% |
| Perfume | 0.5% |

The composition was prepared by fusing the acids in water, adding the triethanolamine, cooling and adding the other constituents. To the mixture was then added 0.5% of n-propyl 2-methylnon-3-yl sulphoxide. The composition was then packaged in an aerosol dispenser under pressure of a butane propellant.

When used in shaving a fresh cool sensation was distinctly noticeable on the face.

EXAMPLE 15

Toilet Water

A toilet water was prepared according to the following recipe:

|  |  |
|---|---|
| Denatured ethanol | 75.0% |
| Perfume | 5.0% |
| Water | to 100% |

To the recipe was added 4.0%, based on the total composition, of n-hexyl 2,3-dimethyl but-2-yl sulphoxide.

As with the after shave lotion, a cooling effect was clearly noticeable on the skin well after the termination of any cooling effect attributable to the evaporation of the alcoholic carrier.

EXAMPLE 16

Deodorant Composition

A deodorant composition suitable for formulation and dispensing as an aerosol under pressure of a suitable propellant was formulated according to the following recipe:

|  |  |
|---|---|
| Denatured ethanol | 96.9% |
| Hexachlorophene | 2.0% |
| Isopropyl myristate | 1.0% |
| Perfume | 0.1% |

To the composition was added 3% by weight of n-butyl 3-ethylpent-3-yl sulphoxide. Application of the final composition gave rise to a definite cooling sensation on the skin.

EXAMPLE 17

Hair Shampoo

Sodium lauryl ether sulphate, 10 g, was dispersed in 90 g water in a high speed mill. To the dispersion was added 4.5% by weight of n-butyl 3-methylhept-4-yl sulphoxide. When the hair is washed using the shampoo a fresh, cool sensation is noticed on the scalp.

EXAMPLE 18

Solid Cologne

A solid cologne was formulated according to the following recipe:

|  |  |
|---|---|
| Denatured Ethanol | 74.5% |
| Propylene Glycol | 3.0% |
| Sodium Stearate | 5.0% |
| Perfume | 5.0% |
| Water | to 100% |

The sodium stearate was dissolved by stirring in a warm mixture of the ethanol, propylene glycol and water. To the solution was added the perfume and 4.0% of sec.butyl 2,6-dimethylhept-4-yl sulphoxide and the mixture then allowed to solidify into a waxy cake.

When applied to the forehead a distinct cooling effect is noticeable.

EXAMPLE 19

Mouthwash

A concentrated mouthwash composition was prepared according to the following recipe:

|  |  |  |
|---|---|---|
| Ethanol | 3.0 | % |
| Borax | 2.0 | % |
| Sodium Bicarbonate | 1.0 | % |
| Glycerol | 10.0 | % |
| Flavourant | 0.4 | % |
| Thymol | 0.03 | % |
| Water | to 100 | % |

To the composition was added 0.2% of n-hexyl 3-methylpent-3-yl sulphoxide.

When diluted with approximately 10 times its own volume of water and used to rinse the mouth a cooling effect is obtained in the mouth.

EXAMPLE 20

Soft Drink

A soft drink concentrate was prepared from the following recipe:

|  |  |
|---|---|
| Pure orange juice | 60% |
| Sucrose | 10% |
| Saccharin | 0.2% |
| Orange flavouring | 0.1% |
| Citric acid | 0.2% |
| Sulphur dioxide | trace amount |
| Water | to 100% |

To the concentrate was added 0.05% of methyl hex-3-yl sulphoxide.

The concentrate was diluted with water and tasted. An orange flavour having a pleasantly cool after-effect was obtained.

EXAMPLE 21

Boiled Sweet 99.5% sucrose and 0.5% citric acid were carefully fused together in the presence of a trace of water. Just before casting the melt onto a chilled plate 0.1% of di-sec.butyl sulphoxide was rapidly stirred in. The melt was then cast. A boiled sweet resulted having a marked cooling effect on the mouth.

EXAMPLE 22

Indigestion Tablet

The following ingredients were ground together:

| | |
|---|---|
| Magnesium carbonate | 49.5% |
| Sorbitol | 49.4% |
| Saccharin | 0.1% |
| Talc | 1.0% |

Added to the mixture during grinding was 0.1% of β-hydroxyethyl hept-3-yl sulphoxide. After mixing the mixture was pressed into 0.5g tablets.

Taken by mouth and swallowed the tablets produced, after a short interval of time, a noticeable cooling effect in the stomach.

EXAMPLE 23

Cleansing Tissue

A cleansing liquid was prepared having the formulation:

| | | |
|---|---|---|
| Triethanolamine Lauryl Sulphate | 1.0 | % |
| Glycerol | 2.0 | % |
| Perfume | 0.95 | % |
| Water | to 100 | % |

To this liquid was added 4% of n-hexyl 3-methylpent-3-yl sulphone. A paper tissue was then soaked in the liquid.

When the impregnated tissue was used to wipe the skin a fresh cool sensation developed on the skin after a short interval.

EXAMPLE 24

Hydrophilic Ointment

A hydrophilic ointment was prepared having the following formulation:

| | |
|---|---|
| Propylene Glycol | 12% |
| 1-Octadecanol | 25% |
| White Soft Paraffin | 25% |
| Sodium Lauryl Sulphate | 1% |
| Water | to 100 |

The sodium lauryl sulphate was added to the water and heated to 60° C. The paraffin was melted by heating to 60° C and was then added to the sodium lauryl sulphate mixture with stirring. Propylene glycol and 1-octadecanol were then added to this mixture.

To the resultant mixture was added 3% of 1-ethylbutyl 3-methylpent-3-yl sulphoxide. The final ointment when applied to the skin gave rise to a marked cooling effect.

EXAMPLE 25

Liniment

A liniment was prepared according to the following formulation:

| | |
|---|---|
| Methyl Salicylate | 25% |
| Eucalyptus Oil | 10% |
| Arachis Oil | to 100% |

To the composition was added 4% of n-propyl 2-methylnon-3-yl sulphoxide.

When the final composition was applied to the skin a clearly noticeable cooling effect became apparent after a short interval of time.

EXAMPLE 26

Toothpick

The tip of a wooden toothpick was impregnated with an alcoholic solution containing n-hexyl 2,3-dimethylbut-3-yl sulphoxide in an amount sufficient to deposit on the toothpick 0.10 mg. of the sulphoxide. The impregnated toothpick was then dried. When placed against the tongue, a cooling effect is noticed after a short period of time.

The above Examples illustrate the range of compounds and the range of compositions included in the invention. However, they are not to be taken as limiting the scope of the invention in any way. Other compounds within the general formula will be equally suitable for use in the compositions of Examples 1–26 and the physiological effect obtained with the compounds of the invention will recommend their use in a wide variety of other compositions where the cooling effect will be of value.

We claim:

1. In a personal care product for topical application to the human body, comprising a topically administrable vehicle and, as adjuvants in said vehicle, i) an antiseptic or odourant or both, and ii) a compound capable of stimulating the cold receptors of the nervous system in the surface tissues of the body when brought into contact therewith by topical application of the said product, the improvement which comprises using as said cold receptor stimulating compound an effective amount of a cold receptor stimulating acyclic sulfoxide or sulfone of the formula:

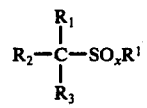

wherein
$R_1$ is H or $C_1$–$C_5$ alkyl;
$R_2$ is $C_1$–$C_6$ alkyl;
$R_3$ is $C_1$–$C_8$ alkyl;
$R_1$, $R_2$ and $R_3$ together provide a total of from 3–15 carbon atoms;
$R^1$ is $C_1$–$C_8$ alkyl;
$R_1$, $R_2$, $R_3$ and $R^1$ together provide a total of from 6–18 carbon atoms; and
$x$ is an integer from 1–2 inclusive.

2. A product according to claim 1 wherein the cold receptor stimulant is of the formula defined in which $R^1$ is alkyl containing up to 8 carbon atoms, $R_1$ is H or $C_1$–$C_4$ alkyl and $R_2$ and $R_3$ are each $C_1$–$C_6$ alkyl, $R^1$, $R_1$, $R_2$ and $R_3$ together providing a total of from 8–14 carbon atoms inclusive.

3. A product according to claim 1, which is a toilet lotion comprising an aqueous, alcoholic or aqueous alcoholic base and, as adjuvants therein, i) an antiseptic or odourant or a mixture thereof, and ii) said cold receptor stimulant.

4. A product according to claim 1, which is a cosmetic preparation comprising an oil-in-water emulsion base, and, as adjuvants in said base, i) at least one of an antiseptic or odourant and ii) said cold receptor stimulant.

5. A product according to claim 1, which is a shaving preparation comprising a foamable base containing a soap or synthetic surfactant and, as adjuvants in said base, (i) a perfume or antiseptic or mixture thereof and (ii) said cold receptor stimulant.

6. A method of stimulating the cold receptors of the nervous system of the surface tissues of the body which comprises contacting the receptors with an effective amount of a cold receptor stimulating sulfoxide or sulfone of the formula:

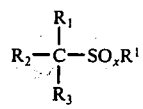

wherein
$R_1$ is H or $C_1-C_5$ alkyl;
$R_2$ is $C_1-C_6$ alkyl;
$R_3$ is $C_1-C_8$ alkyl;
$R_1$, $R_2$ and $R_3$ together provide a total of from 3-15 carbon atoms;
$R^1$ is $C_1-C_8$ alkyl;
$R_1$, $R_2$, $R_3$ and $R^1$ together provide a total of from 6-18 carbon atoms; and
$x$ is an integer from 1-2 inclusive.

* * * * *